United States Patent
Wen et al.

(10) Patent No.: US 11,578,365 B2
(45) Date of Patent: Feb. 14, 2023

(54) CHICKEN WHOLE-GENOME SNP CHIP AND USE THEREOF

(71) Applicant: INSTITUTE OF ANIMAL SCIENCE, CHINESE ACADEMY OF AGRICULTURAL SCIENCES, Beijing (CN)

(72) Inventors: Jie Wen, Beijing (CN); Ranran Liu, Beijing (CN); Guiping Zhao, Beijing (CN); Maiqing Zheng, Beijing (CN); Qinghe Li, Beijing (CN); Huanxian Cui, Beijing (CN); Siyuan Xing, Beijing (CN)

(73) Assignee: INST. OF ANIMAL SCI., CHINESE ACAD. OF AG. SCIENCE, Beijing (CN)

( * ) Notice: Subject to any disclaimer, the term of this patent is extended or adjusted under 35 U.S.C. 154(b) by 0 days.

(21) Appl. No.: 16/309,763

(22) PCT Filed: Oct. 10, 2017

(86) PCT No.: PCT/CN2017/105438
§ 371 (c)(1),
(2) Date: Dec. 13, 2018

(87) PCT Pub. No.: WO2019/071407
PCT Pub. Date: Apr. 18, 2019

(65) Prior Publication Data
US 2021/0139962 A1    May 13, 2021

(51) Int. Cl.
*C12Q 1/6876* (2018.01)
*A01K 67/00* (2006.01)
*A01K 67/027* (2006.01)

(52) U.S. Cl.
CPC ............ *C12Q 1/6876* (2013.01); *A01K 67/00* (2013.01); *A01K 67/0275* (2013.01); *C12Q 2600/124* (2013.01); *C12Q 2600/156* (2013.01)

(58) Field of Classification Search
None
See application file for complete search history.

(56) References Cited

FOREIGN PATENT DOCUMENTS

| | | |
|---|---|---|
| CN | 1438325 A | 8/2003 |
| CN | 102747138 A | 10/2012 |
| CN | 105238859 A | 1/2016 |
| CN | 111225986 B | 2/2021 |

OTHER PUBLICATIONS

Kranis et al; BMC Genomics; 14:59, pp. 1-13, 2013.*
Granted Claims for Chinese Application No. 201780023241.X.
Notification of the First Office Action for Chinese Application No. 201780023241.X dated Oct. 30, 2020.
Notification to Grant Patent Right for Invention for Chinese Application No. 201780023241.X dated Jan. 12, 2021.
Search Report for Chinese Application No. 201780023241.X dated Oct. 23, 2020.
Ailuan, et al., "Status and Prospect of Whole-genome Association Analysis of Chicken Important Traits", Chinese Poultry, vol. 39, Issue 18, 2017, pp. 1-6.

* cited by examiner

*Primary Examiner* — Jehanne S Sitton
(74) *Attorney, Agent, or Firm* — Dorsey & Whitney LLP

(57) ABSTRACT

Provided in the present invention is a chicken whole-genome SNP chip and application thereof. There are a total of 50,000 SNP loci on the chip: including 19,600 SNP loci for white-feather broilers, yellow-feather and partridge chickens having a MAF value greater than 0.05 and uniformly distributed across the genome which were derived from the data of the whole-genome resequencing of main indigenous chicken breeds in China and introduced chicken breeds; 14,000 SNP loci associated with economic traits, and 16,400 SNP loci for making up for the genomic regions that are not covered by the first two types of probes. The 50,000 SNP loci on the chicken whole-genome SNP chip of the present invention have DNA sequences represented by SEQ ID NOs. 1 to 50,000. The SNP loci on the chip are uniformly distributed across the whole genome, and associated with traits such as feed efficiency, meat production rate, lipid metabolism, meat quality, general resistance to diseases, reproduction and the like, and the chip has moderate through-put and low cost, and could be used universally for chicken breeds at indigenous and abroad.

1 Claim, 2 Drawing Sheets

Specification includes a Sequence Listing.

CHICKEN WHOLE-GENOME SNP CHIP AND USE THEREOF

SEQUENCE LISTING

A sequence listing submitted in computer readable format is hereby incorporated by reference. The computer readable file, created 25 Mar. 2022 is named KHP183110201_7_the_amended_Sequence_Listing.txt and is 13,778,625 bytes in size.

CROSS-REFERENCE TO RELATED APPLICATIONS

The present application is the U.S. National Phase filing under 35 U.S.C. § 371 of International Application No. PCT/CN2017/105438, filed Oct. 10, 2017, the content of which is herein incorporated by reference in its entirety.

TECHNICAL FIELD

The present invention relates to the fields of molecular biology, functional genomics, bioinformatics and genome breeding, and more particularly relates to a chicken whole-genome SNP chip and application thereof.

BACKGROUND ART

Single nucleotide polymorphism (SNP) refers to the variation of a single nucleotide in a genome, which is a form of variation formed by substitution, transversion, insertion or deletion of a single nucleotide pair. As a third-generation genetic marker, the single nucleotide polymorphisms are numerous, densely distributed, and easy to detect, and are relatively ideal genotyping targets.

A whole-genome SNP chip is a SNP microarray, also known as SNP array, with millions of DNA marker sequences aligned and immobilized to form an array of SNP probes on a slide or a special silicon wafer. It works by means of base-pairing reaction of the DNA marker sequences immobilized on the chip with the target genome so as to accurately identify the genetic information. The gene chip uses advanced microbiochemical reaction technology, micro-labeling technology, micro-scale scanning resolution imaging technology and biological information computer processing technology to accurately identify specific mRNA or DNA sequences in biological subjects. Currently, there are two US biotech companies, ThermoFisher and Illumina, each having a commercial genome SNP chip manufacturing technical platform. ThermoFisher (formerly Affymetrix) uses the Axiom platform technology to manufacture a SNP chip (www.thermofisher.com), i.e., in-situ photolithographic technology is used to in-situ synthesize gene probe sequences on a substrate by photolithography. The chip has been widely used in the study of animal and plant genome variations.

The livestock and poultry whole-genome SNP chip can be applied to the fields of molecular genetic research and molecule-assisted breeding and the like because of its advantages, such as high marker density, uniform coverage of the whole genome, high measurement accuracy, easy realization of standardization and automated detection, etc. It can provide support for upstream and downstream processes of breeding, including genetic diversity analysis of genetic resources, genetic relationship analysis, genome-wide association analysis (GWAS), QTL (quantitative trait locus) mapping analysis, selective evolution studies and the like, wherein a very important use is the use in genomic selection breeding. Genomic selection is currently the main breeding technique in livestock and poultry breeding, using whole-genome markers to estimate all possible genetic effects, and interpret all genetic variations, so as to predict Genomic Estimated Breeding Values (GEBVs) through statistically labeled genetic effects. Genomic selection has the advantages of high accuracy of estimated breeding values and rapid genetic progress. It has been applied to the breeding practice of commercialized lines of dairy cows, pigs, abroad high-yielding layers and fast growing white-feather broilers.

However, the loci information of the current chicken 600K commercial SNP chip (Axiom® Whole-genome Chicken Genotyping Array) mostly derived from abroad commercial layers and broilers, lacking the genome variation information of Chinese indigenous chicken breeds (meat-type breeds or high-quality layer chicken breeds), and there are great limitations in the application in Chinese indigenous chicken breeding and related basic scientific research. Moreover, compared with other animals, chickens have the characteristics of numerous breeds and large population, but low individual price and the like, therefore, a relatively low-cost whole-genome SNP chip is needed for large population sample testing. Thus, broiler and laying hen breeding industry and scientific research fields urgently need to develop a whole-genome SNP chip with moderate flux, including specific information on the genetic variation of Chinese indigenous chicken breeds, and taking into account the genomic information of chicken breeds introduced from abroad.

SUMMARY OF THE INVENTION

One purpose of the present invention is to provide a chicken whole-genome SNP chip and application thereof.

The present invention first provides a combination of chicken whole-genome SNP molecular markers consisting of 50,000 SNP/INDEL molecular markers, the nucleotide sequences of which are represented by SEQ ID NOs. 1 to 50,000, respectively.

The present invention provides a chicken whole-genome breeding chip comprising 50,000 SNP/INDEL molecular markers having the nucleotide sequences represented by SEQ ID NOs. 1 to 50,000.

In the above combination of chicken whole-genome SNP molecular markers and the above chicken whole-genome breeding chip of the present invention, the SNP/INDEL loci of the molecular marker is located at the $36^{th}$ position of the nucleotide sequences represented by SEQ ID NOs. 1 to 50,000.

The molecular markers are associated with chicken functional traits, The traits are as follows: growth traits including feed efficiency and body weight of different day-ages; carcass traits including breast muscle weight percentage (BMP), leg muscle weight percentage (LMP), total weight percentage after slaughtering (TWP), and abdominal fat percentage (AbFP); immune traits including IgY levels in serum, IgY levels in response to sheep red blood cell (SRBC), the heterophil and lymphocyte ratio (H/L), and the average red blood cell backlog (ABRBC); meat quality traits including the ultimate pH, breast muscle intramuscular fat ratio (IMFbr), meat lightness, yellow value and red value; and reproductive traits.

The present invention provides the above chicken whole-genome breeding chip which is suitable for chicken breeds at indigenous and abroad, named as IASCHICK chicken SNP chip, and has stronger correlation with economic traits and moderate through-put. The SNP loci on this chip include three types: the first type is derived from the information of the whole-genome resequencing of five indigenous breeds and three introduced chicken breeds, which are frequently used in domestic meat-type chicken breeding. The indigenous breeds resequenced include yellow-feather broilers and partridge chickens and the like. After filtering, there are 19,600 SNPs (referred to as the first type of probes in the present chip) having a minor allele frequency (MAF) value greater than 0.05 and uniformly distributed across the genome were screened out from white-feather broilers, yellow-feather chickens and partridge chickens. The second type of SNPs includes 14,000 SNPs (referred to as the second type of probes in the present chip) associated with economic traits, which were screened out by a variety of correlation analysis such as genome-wide association analysis. The third type includes 16,400 probes (referred to as the third type of probes in the present chip) from SNPs of existing databases used to make up for the genomic regions that cannot be covered by the above two types of probes.

Specifically, the first type of probes includes 12,600 white-feather chicken SNPs, 4,000 yellow-feather broiler SNPs, and 3,000 partridge broiler SNPs. The second type of probes includes 6,000 significant loci obtained from genome-wide association analysis of total 15 traits (including growth, meat quality, disease resistance and reproduction) by using F2 hybrid populations of indigenous breeds and introduced breeds and the like as materials and using illumina 60K SNP Bead Chip. By comparison among multiple control lines, 3,000 SNPs in the corresponding regions of 100 candidate genes (related to traits such as fat deposition and the like) were obtained. A total of 5,000 SNPs of economic trait-related genes were obtained by searching previous research results.

Among the 50,000 loci in the entire chip, 17,000 are newly discovered by resequencing of multiple breeds, and are SNPs not listed in the Ensembl chicken variation database. The IASCHICK chip was fabricated by designing probes for the total 50,000 loci and performing in-situ photolithography synthesis process with ThermoFisher's Axiom platform technology. Each chip can be used to simultaneously detect 96 or 384 samples.

The 50,000 SNPs obtained by the present invention have the DNA sequences and characteristics represented by SEQ ID No. 1 to SEQ ID No. 50,000. The IASCHICK chicken whole-genome SNP chip according to the present invention refers to a chip fabricated by in-situ photolithography synthesis process based on the 50,000 sequences using ThermoFisher's Axiom platform technology. The SNP/INDEL loci on the IASCHICK chicken whole-genome SNP chip of the present invention refers to the nucleotide at the $36^{th}$ position in the sequence represented by SEQ ID No. 1 to SEQ ID No. 50,000.

The present invention also provides the use of the above chicken whole-genome SNP chip—IASCHICK chicken SNP chip in detecting chicken DNA samples. The chip can be used in applications such as evaluation of germplasm resources for indigenous and abroad chicken breed resources, whole-genome selection breeding of indigenous broilers and layers, identification of QTLs, association loci and candidate genes for target trait, genetic relationship analysis and the like.

Specifically, the present invention provides the use of the above combination of chicken whole-genome SNP molecular markers and/or the above chicken whole-genome breeding chip in improving chicken germplasm resources.

The present invention provides the use of the above combination of chicken whole-genome SNP molecular markers and/or the above chicken whole-genome breeding chip in identifying chicken breeds.

The present invention provides the use of the above combination of chicken whole-genome SNP molecular markers and/or the above chicken whole-genome breeding chip in chicken breeding.

The present invention provides the use of the above combination of chicken whole-genome SNP molecular markers and/or the above chicken whole-genome breeding chip in identifying chicken genetic relationships.

The present invention provides the use of the above combination of chicken whole-genome SNP molecular markers and/or the above chicken whole-genome breeding chip in analyzing chicken genetic diversity.

The present invention provides the use of the above combination of chicken whole-genome SNP molecular markers and/or the above chicken whole-genome breeding chip in chicken genome-wide association analysis.

The present invention has the following advantages: (1) the present invention has three characteristics: first, it may be used universally for indigenous and abroad chicken breeds: the characteristic loci of the representative Chinese indigenous chicken breeds and highly-selected commercial chicken breeds at indigenous and abroad were comparatively screened to ensure the universality and effectiveness of the loci information. Second, it has functional correlation with economic traits. The loci having significant genetic association with traits such as feed efficiency, meat production rate, lipid metabolism, meat quality, general disease resistance, and reproduction were screened out, so as to increase the accuracy of the basic researches performed using the chip. Third, the loci are uniformly distributed and the throughput is moderate. The 50,000 loci are uniformly distributed across the whole genome (except that the density on chromosome 16 is relatively high), with an average interval of 24 kb (kilobase), thereby ensuring the accuracy of the breeding value estimation and related researches. Compared with the existing 600K commercial chip, the throughput is moderate, the price is greatly reduced, and the cost performance is high. (2) Compared with the genotyping system based on the second-generation resequencing, the data analysis is simple and it is easy to implement standardized and automatic detection and analysis, and it is relatively easy to achieve comparability among different batches and different laboratory data, since the variant loci to be detected are fixed.

SPECIFIC MODES FOR CARRYING OUT THE EMBODIMENTS

Figure 1:
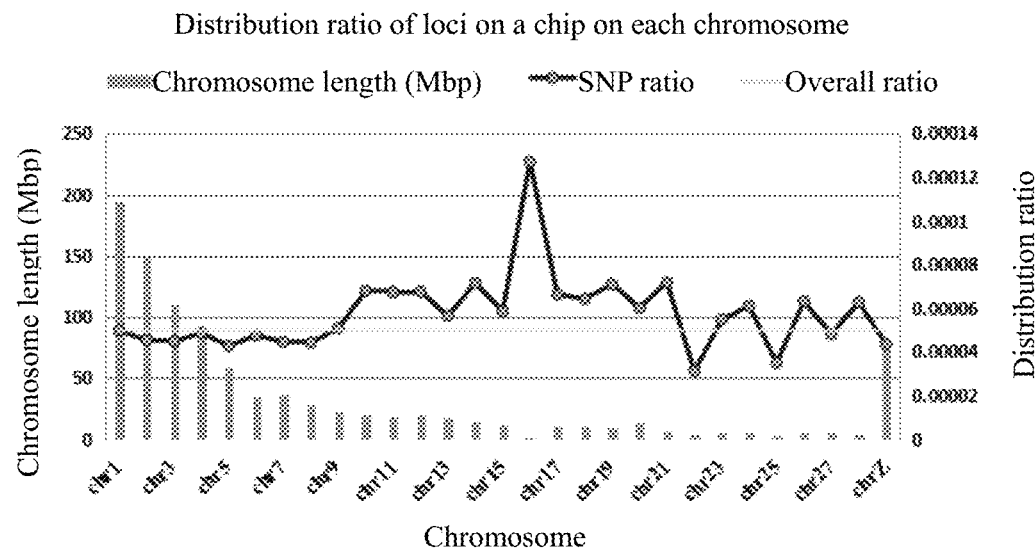
FIG. 1 shows that the 50K loci are uniformly distributed across the whole chromosome (except for chromosome 16) and have similar LD levels.

The following Examples are intended to further illustrate the present invention, but are not intended to limit the scope of the present invention. Modifications or substitutions of the methods, steps or conditions of the present invention made without deviating from the spirit and substance of the present invention fall within the scope of the invention.

The technical means used in the Examples are conventional means well known to a person skilled in the art unless otherwise specified.

Example 1: Method for Preparing an IASCHICK Chicken Whole-Genome SNP Chip

1. Acquisition of the first type of probes: The first type of probes was mainly characterized by obtaining 50,000 specific SNP loci for Chinese indigenous chicken breeds for breeding purpose and abroad fast-growing white-feather broilers.

First, eight indigenous and abroad chicken breeds (see Table 1) were subjected to whole-genome resequencing using the Hiseq 2500 platform (Illumina Inc.) sequencing technology and a 20-fold genomic coverage was obtained for each sample. The specific procedure comprised constructing a sequencing library for each breed, and the specific construction method comprised setting up three mixing pools for each breed, and constructing a DNA library using the standard procedure for Nextera DNA library preparation kit (Illumina Inc., San Diego, Calif., USA). All DNA libraries were sequenced on the Hiseq 2500 platform. Low-quality (fragment length <10) reads and adapter-polluted reads were eliminated so as to obtain clean data. All clean data were mapped to GalGAL 4.0 (Li and Durbin, 2010) by BWA tools software, and PCR duplication was removed using the rmdup parameter in SAM tools (Li et al., 2009). SNP mutation typing was performed using the mpileup function of SAM Tools software (Koboldt et al., 2009). A total of 15,312,402 high-quality mutation loci were obtained (see Table 1). The loci with a minor allele frequency value greater than 0.05 were used as data sources for the first type of probes. In addition, the procedure further comprised target region sequence capture and resequencing of chromosomes 11, 16 and 19 of high and low IgY group samples of Leghorns and Beijing-You chicken, and as a result, 1,700 related high-quality mutation loci were obtained.

TABLE 1

Indigenous and abroad chicken breeds for resequencing and the number of identified SNPs

| Breeds | | SNP/Ten thousand |
|---|---|---|
| Yellow feather | Beijing-You chicken | 850.5214 |
| | Yellow dwarf chicken | 834.9627 |
| | Sanhuang chicken | 940.5319 |

TABLE 1-continued

Indigenous and abroad chicken breeds for resequencing and the number of identified SNPs

| Breeds | | SNP/Ten thousand |
|---|---|---|
| Cyan-shank partridge | Cyan-shank partridge chicken (fast-growing) | 895.4795 |
| | Cyan-shank partridge chicken (medium-growing) | 888.4232 |
| Introduced white feather | Cobb maternal line | 709.3225 |
| | Cobb paternal line | 837.2769 |
| | Recessive white chicken | 755.6464 |
| | Total | 15312402 |

2. Acquisition of the second type of probes: SNP loci associated with 15 target traits were obtained based on genome-wide association analysis (GWAS) and screening methods for SNPs in related candidate genes.

First, the F2 chicken resource population (the Chinese Academy of Agricultural Sciences) produced by the hybridization between Beijing-You chicken and Cobb chickens were used. A total of 400 chickens including F0-F2 generations were used. Phenotypic assays were well known methods, including (1) breast muscle weight percentage, leg muscle weight percentage, total weight percentage after slaughtering and abdominal fat percentage, body weight at the age of 28 days, body weight at the age of 42 days; (2) IgY levels in response to sheep red blood cell (SRBC), IgY levels in serum, H/L value, and the average red blood cell backlog (ABRBC); and (3) the ultimate pH, breast muscle intramuscular fat ratio (IMFbr), meat lightness, yellow value and red value. Venous blood samples were collected from wings of test chickens for genomic DNA extraction. The Illumina chicken 60K whole-genome SNP chip was used for assay, and after quality control, there were 42,585 remaining SNP loci. The GLM model in the plink software was used for genome-wide association analysis, and after the p-value was corrected by the Bonferroni method, 6,147 loci with the top one percent significance for the 15 main traits such as body weight at the age of 42 days, IMFbr and IgY levels in serum and the like were obtained and used as candidate loci.

Screening method for candidate genes: economic trait-related candidate genes were obtained based on the applicant's previous research and PUBMED database on the NCBI website (see Table 2), and in combination with the resequencing results in Example 1, the SNP loci located within the target gene and downstream and upstream of the target gene were obtained. Each gene has more than 100 SNPs as candidate. 15,173 candidate SNP loci were obtained by removing the repeated loci and screening based on the locus's minor allele frequency (MAF<0.05) and the annotation on the location of the loci in the gene structure (preferentially intragenic and regulatory regions).

TABLE 2

Data Sources for the second type of probes

| Traits | Gene number | SNP | SNP/Per gene | References |
|---|---|---|---|---|
| Various economic traits | 48 | 7,224 | 151 | Obtained by searching in PUBMED with chicken and gene and/or polymorphism as keywords |
| Genes in QTL regions of various economic traits | 880 | 94,000 | 106 | Obtained by searching in PUBMED with chicken and QTL as keywords |
| Muscle development | 310 | 42,470 | 137 | Cui et al., BMC Genomics. 2012, 13: 213; Wang Hongyang. "Proteomics study of muscle development and intramuscular fat deposition in chickens from embryonic period to early growth period" |

TABLE 2-continued

Data Sources for the second type of probes

| Traits | Gene number | SNP | SNP/Per gene | References |
|---|---|---|---|---|
| Lipid Metabolism | 333 | 51,282 | 154 | Huang et al., Scientific Reports. 2015, 5: 16132 Sun et al., BMC Genomics, 2013. 14: 458. etc. |
| Salmonella, influenza resistance, and resistance to general disease | 297 | 33,876 | 111 | Peng Li, et al., Veterinary Microbiology 2010, 143: 346-351; Qinghe Li, et al., Journal of Proteomics, 2016, 148: 20-25 |
| Total | 1868 | 228,852 | >100 | |

The final procedures for determining loci for the chip were as follows:

(1) After the first and second types of probes were sent to the Thermo company for scoring, the loci for which probes are not recommended to design were removed;

(2) Chromosomes were divided with a window/interval of 24 kb, the SNP in the second type of probes was preferentially selected for each interval and in case of lacking the second type of probes, the SNP in the first type of probes was selected. The probes for regions that were still not covered after the first and second types of probes were selected were obtained from the SNPdb database on the NCBI website (www.ncbi.nlm.nih.gov/projects/SNP/index.html).

Finally, 50,000 SNPs with uniform distribution across the whole genome (except that the density on chromosome 16 was relatively high, as shown in FIG. 1, Table 3) was achieved. The chip had (1) versatility: the characteristic SNPs of indigenous chicken breeds and commercially introduced breeds were contained; (2) effectiveness: the MAF of 20K loci in 8 indigenous and abroad chicken breeds (such as white-feather, yellow-feather, partridge chicken, etc.) was all higher than 0.05; (3) functional correlation: 14K loci were identified by GWAS and other studies as being associated with economic traits, such as growth, carcass composition, meat quality, general immunity, reproduction, appearance, etc.; and (5) moderate throughput: 50,000 SNP loci were uniformly distributed across the whole genome at an average interval of 24 kb, and the application performance/price ratio is high in the practice of whole-genome selection breeding.

TABLE 3

The number of loci on the chip distributed in each chromosome

| Chromosome | SNP number |
|---|---|
| chr1 | 9,752 |
| chr2 | 6,752 |
| chr3 | 4,961 |
| chr4 | 4,392 |
| chr5 | 2,552 |
| chr6 | 1,664 |
| chr7 | 1,618 |
| chr8 | 1,275 |
| chr9 | 1,194 |
| chr10 | 1,354 |
| chr11 | 1,307 |
| chr12 | 1,344 |
| chr13 | 1,005 |
| chr14 | 1,085 |
| chr15 | 743 |
| chr16 | 68 |
| chr17 | 699 |
| chr18 | 722 |
| chr19 | 709 |

TABLE 3-continued

The number of loci on the chip distributed in each chromosome

| Chromosome | SNP number |
|---|---|
| chr20 | 849 |
| chr21 | 493 |
| chr22 | 148 |
| chr23 | 317 |
| chr24 | 384 |
| chr25 | 102 |
| chr26 | 336 |
| chr27 | 272 |
| chr28 | 312 |
| chrZ | 3,591 |
| Total | 50,000 |

Example 2: Method of Applying IASCHICK Chicken SNP Chip in Detection of Chicken DNA Samples Chicken blood samples were collected, the genomic DNA of the blood was extracted by a phenol-chloroform method or a special kit and dissolved in ddH$_2$O, and the purity was checked by 1% agarose gel electrophoresis. DNA sample quality detection: agarose gel electrophoresis with a mass fraction of 1% to 1.5% (w/w) was used for detection, the gel imaging system (GelDocXR System, Bio-Rad company, USA) was used to determine the electrophoresis results to ensure good integrity of genomic DNA and a length of the genomic DNA fragment greater than 10 kb; the concentration of genomic DNA was measured by a micro-ultraviolet spectrophotometer (Q5000, Quayu company, USA) or a similar nucleic acid protein analyzer, and the DNA concentration was adjusted to a working concentration of 10 to 50 ng/µl.

Gene chip detection: operation was performed according to the standard process for Affymetrix GeneTitan™ gene chip assay (Axiom 2.0 Target Prep 384 Samples Protocol www.thermofisher.com). The chip scanning was performed using a GeneChip HT Array Plate Scanner chip scanner (GeneChip HT Array Plate Scanner, Thermos Fisher Scientific company, USA).

Data Analysis: Genotypes were analyzed using Axiom Analysis Suite (software download www.thermofisher.com/cn/zh/home/life-science/microarray-analysis/microarray-analysis-instruments-software-services/microarray-analysis-software/axiom-analysis-suite.html, source of the software: www.thermofisher.com), and the R language (www.rproject.org) was used for programming so as to obtain genotype comparison results.

Example 3: Mining of Important Economic Trait-Related Genes was Performed Based on Test Results with IASCHICK Chicken SNP Chip The 1062 random selected individuals of the fast-growing white-feather broiler K line were subjected to IASCHICK chip detection (performed according to the method of Example 2), with the quality control conditions for genotype: individual call rate (CR)>95%, MAF>0.05, Hardy-Weinberg equilibrium test >0.001. After quality control, 948 qualified individuals and 46,386 high-quality SNP loci were obtained for GWAS analysis. The GWAS analysis based on the mixed linear model was performed according to the calculation results (between −46.77 and 22.80) of the corresponding residual feed intake (RFI) of individuals (28 to 42 days old). With $p<1\times10^{-5}$ as the genome-related level, loci exhibiting significant association were obtained, as shown in Table 4. There were four loci significantly associated with RFI in the region of 51526729-66784053 bp of No. 1 chromosome, 15.3 Mb in total, suggesting that this region is a key QTL region affecting RFI. Moreover, this region contains the IGF-1 gene (Chr1: 55335204-55383631 bp), which gene has been proved to be a known gene affecting growth and feed efficiency. Loci showing significant association on chromosomes 2, 4, 7 and 10 may be previously undiscovered variants. Therefore, the IASCHICK chip prepared in Example 1 was used to identify the genotype to obtain data, and a relatively accurate association analysis result can be obtained, as shown in Table 4.

feather broilers including Hubbard broiler and synthetic white-feather broiler K line. The indigenous chicken breed samples were collected from the National Poultry Genetic Resources of the Institute of Poultry Research of the Chinese Academy of Agricultural Sciences, respectively 20 birds for each breed. Among the tested 10 chicken breeds, the detection rate of all SNP loci was 97% or more, and the loci having a MAF greater than 0.05 were more than 40,000, accounting for more than 80%. The mean MAF within breeds was between 0.22 and 0.27. It is proved that the IASCHICK chicken SNP chip loci are widely applicable to indigenous and abroad chicken breeds, and there was a high polymorphism in both indigenous breeds and introduced breeds.

Figure 2:
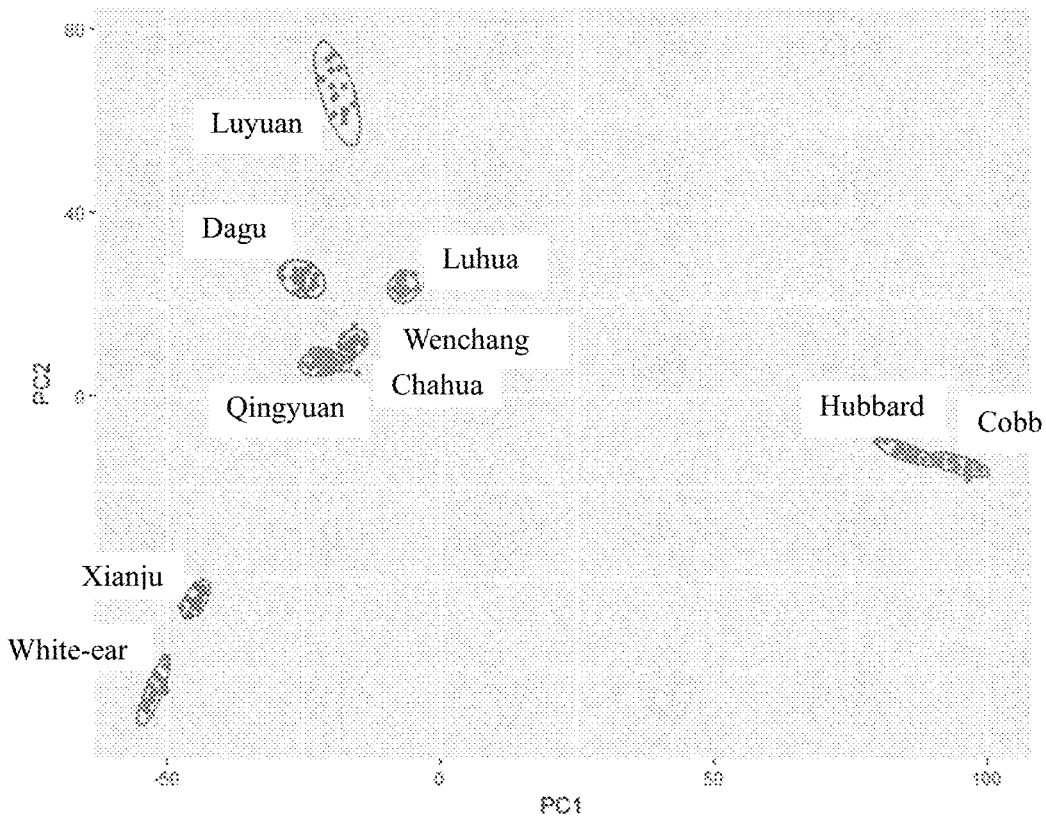
FIG. 2 is a graph showing the results of PCA for clustering for indigenous and abroad chicken breeds.

Quality control was performed on the genotype results (for conditions, see the method of Example 3). Cluster analysis was performed respectively using the PCA population structure and the MEGA software's neighbor-joining method (NJ), and the results were consistent. The PCA results were shown in FIG. 2 (the MEGA results were not given). For small-sized indigenous meat-type chicken breeds, the Chahua chickens and Qingyuan chickens have the closest distance, the next being the small-sized meat-type Wenchang chicken; and for large-sized meat-type chicken breeds, Luhua chickens, Luyuan chickens, and Dagu chickens were respectively clustered into one category. Moreover, as a whole, the meat-type chicken breeds have a closer distance than the egg-type chicken breeds and the introduced fast-growing and large-sized white-feather

TABLE 4

Information table of loci showing significant association obtained by GWAS analysis for RFI trait

| SNP name | Chromosome | Chromosome position (bp) | Upstream and downstream adjacent gene | Distance (kb) | P_value |
| --- | --- | --- | --- | --- | --- |
| AX_172568278 | 1 | 51425729 | CYTH4 | within | 9.64E−07 |
| AX_172566576 | 1 | 51425733 | CYTH4 | within | 9.65E−07 |
| AX_75478420 | 1 | 56132680 | CHPT1; ATP6V0A4 | 488; 251 | 2.81E−06 |
| AX_172675091 | 1 | 59382649 | DNM1L; MIR6700 | 376; 30 | 1.02E−06 |
| AX_75501099 | 1 | 66784053 | C3AR1; ST8SIA1 | 63; 27 | 9.64E−07 |
| AX_75531923 | 1 | 82792277 | QTRTD1 | 212 | 9.64E−07 |
| AX_75322007 | 1 | 164057964 | — | — | 9.72E−07 |
| AX_172592895 | 2 | 129826402 | AZIN1; NCALD | 14; 283 | 3.42E−07 |
| AX_80976861 | 4 | 37059652 | HPGDS | 390 | 9.39E−07 |
| AX_76675177 | 4 | 48727906 | MIR1730 | 193 | 6.48E−06 |
| AX_172565228 | 7 | 27104939 | ADCY5 | within | 4.73E−06 |
| AX_172565235 | 7 | 27466345 | MYLK | within | 4.45E−06 |
| AX_172579026 | 7 | 27720431 | UMPS | 292 | 2.66E−06 |
| AX_75614475 | 10 | 5811559 | MCEE; TARSL2 | 68; 341 | 9.64E−07 |

Example 4: Wide Applicability of Detection with IASCHICK Chips for Indigenous and Abroad Chicken Breeds and Results of Genetic Diversity Analysis of Indigenous Chicken Breeds The present invention uses the IASCHICK chicken chip prepared in Example 1 to carry out genetic diversity analysis on 8 indigenous chicken breeds and 2 fast-growing white feather chicken breeds (performed according to the method of Example 2). Indigenous chicken breeds include meat-type chickens comprising Qingyuan chicken, Wenchang chicken, Chahua chicken, Luhua chicken, Luyuan chicken, and Dagu chicken; egg-type chickens including white-ear chicken and Xianju chicken; and commercialized fast-growing white-broilers. For the egg-type indigenous chicken breeds, the white-ear chicken and Xianju chicken have the closest distance, and were distinguished from various meat-type indigenous chicken breeds; and the introduced abroad fast-growing and large-sized white-feather Hubbard broiler and the synthetic fast-growing and large-sized white-feather broiler K line (which has a genetic connection with the introduced fast-growing and large-sized chicken) had the closest clustering distance and were clearly distinguished from various indigenous chicken breeds. The results show that the IASCHICK chicken SNP chip prepared in Example 1 can be well applied to the diversity and evolution analysis of indigenous chicken germplasm resources, and the identification results were accurate and reliable.

Figure 3:
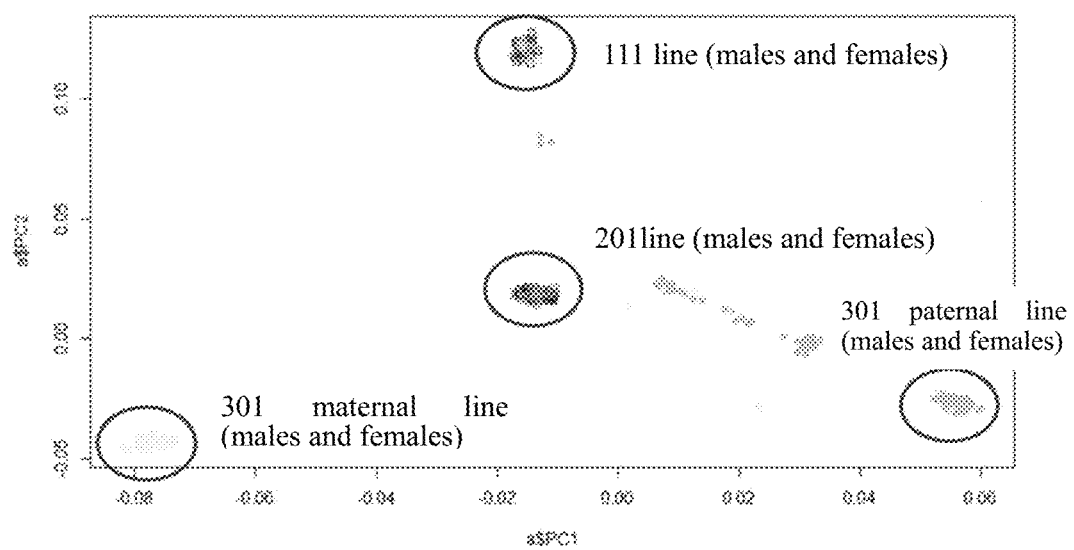
FIG. 3 is a graph showing the results of PCA for clustering for different chicken populations in the same farm.

Example 5: Identification of Genetic Relationship Based on Test Results with IASCHICK Chicken SNP Chip Genetic breeding of chickens is usually carried out for the breeding of large populations under a high selection pressure. In the practice, due to a variety of subjective or objective factors, some chickens may be mixed and the sources cannot be distinguished. Therefore, it is necessary to carry out the identification of genetic relationship of chicken populations. In the present Example, for the populations of three chicken lines doped with non-pure chicken lines in a farm that are to be tested, the IASCHICK chicken SNP chip prepared in Example 1 was used to perform genetic relationship detection on the DNA samples of totally 412 chickens of 111 line, 201 line and 301 lines, and the results according to PCA and MEGA clustering analyses were consistent. The PCA results were shown in FIG. 3 (the MEGA results were not given). There were 67 non-pure chickens (individuals outside the 4 black circles in the figure) were identified, which need to be eliminated or adjusted in the breeding. Other individuals in the black circles belong to 3 known line populations in production. After identification by the IASCHICK chip, the results can assist in the accurate identification of genetic relationship in breeding and accelerate the breeding process.

INDUSTRIAL APPLICABILITY

There are a total of 50,000 SNP loci on the chicken whole-genome SNP chip provided by the present invention: respectively derived from the whole-genome resequencing information of the main Chinese indigenous chicken breeds and introduced chicken breeds, 19,600 SNP loci having MAF greater than 0.05 and uniformly distributed across the genome; 14,000 SNP loci associated with economic traits; and 16,400 SNP loci for making up for the genomic regions that are not covered by the first two types of probes were screened out from white-feather broilers, yellow-feather and partridge chickens. The SNP loci on the chip respectively have the DNA sequences represented by SEQ ID NOs. 1 to 50,000. The SNP loci on the chip are uniformly distributed in the whole genome, and associated with traits such as feed efficiency, meat production rate, lipid metabolism, meat quality, general disease resistance, reproduction and the like, and the chip has moderate throughput and low cost, and may be used universally for indigenous and abroad chicken breeds.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11578365B2). An electronic copy of the "Sequence Listing" will also be available from the USPTO upon request and payment of the fee set forth in 37 CFR 1.19(b)(3).

What is claimed is:

1. A chicken breeding chip comprising a combination of oligonucleotide probes immobilized on the chip, wherein the combination of probes consists of 50,000 oligonucleotide probes, each probe consisting of one of the sequences of SEQ ID NOs 1-50,000, respectively.

* * * * *